(12) United States Patent
Chen et al.

(10) Patent No.: US 12,298,272 B2
(45) Date of Patent: May 13, 2025

(54) NANOPORE-BASED SEQUENCING WITH VARYING VOLTAGE STIMULUS

(71) Applicant: Roche Sequencing Solutions, Inc., Pleasanton, CA (US)

(72) Inventors: Roger J. A. Chen, Saratoga, CA (US); Hui Tian, Cupertino, CA (US); J. William Maney, Jr., Emerald Hills, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 644 days.

(21) Appl. No.: 17/451,283

(22) Filed: Oct. 18, 2021

(65) Prior Publication Data

US 2022/0034839 A1 Feb. 3, 2022

Related U.S. Application Data

(60) Division of application No. 16/238,451, filed on Jan. 2, 2019, now Pat. No. 11,150,216, which is a (Continued)

(51) Int. Cl.
*G01N 27/447* (2006.01)
*B01L 3/00* (2006.01)
(Continued)

(52) U.S. Cl.
CPC .... *G01N 27/44791* (2013.01); *B01L 3/50273* (2013.01); *C12Q 1/6869* (2013.01);
(Continued)

(58) Field of Classification Search
CPC ....... G01N 27/44791; G01N 27/44743; G01N 33/48721; C12Q 1/6869; C12Q 1/6874;
(Continued)

(56) References Cited

U.S. PATENT DOCUMENTS 6,821,730 B2  11/2004  Hannah
7,279,337 B2  10/2007  Zhu
(Continued)

FOREIGN PATENT DOCUMENTS

CN    103298984 A     9/2013
DE    112007001044 T5  4/2009
(Continued)

OTHER PUBLICATIONS

He, Jin et al., Identification of DNA base-pairing via tunnel-current decay, Nno Lett., Nov. 12, 2015, pp. 3854-3858, vol. 7.
(Continued)

*Primary Examiner* — Brian W Cohen
*Assistant Examiner* — Vivian A Tran
(74) *Attorney, Agent, or Firm* — Roche Sequencing Solutions, Inc.

(57) ABSTRACT

A method of analyzing a molecule in a nanopore is disclosed. A voltage is applied across a nanopore that is inserted in a membrane by coupling the nanopore to a voltage source. The nanopore is decoupled from the voltage source. After the decoupling, a rate of decay of the voltage across the nanopore is determined. A molecule in the nanopore is distinguished from other possible molecules based on the determined rate of decay of the voltage across the nanopore.

7 Claims, 11 Drawing Sheets

Related U.S. Application Data continuation of application No. 15/371,106, filed on Dec. 6, 2016, now Pat. No. 10,215,731, which is a continuation of application No. 14/577,511, filed on Dec. 19, 2014, now Pat. No. 9,557,294.

(51) Int. Cl.
*C12Q 1/6869* (2018.01)
*G01N 33/487* (2006.01)

(52) U.S. Cl.
CPC . *G01N 27/44743* (2013.01); *G01N 33/48721* (2013.01); *B01L 2400/0421* (2013.01)

(58) Field of Classification Search
CPC ........ C12Q 2565/629; C12Q 2565/631; B01L 3/50273; B01L 2400/0421
See application file for complete search history.

(56) References Cited

U.S. PATENT DOCUMENTS

| | | |
|---|---|---|
| 7,410,564 B2 | 8/2008 | Flory |
| 8,003,319 B2 | 8/2011 | Polonsky et al. |
| 8,105,846 B2 | 1/2012 | Bayley et al. |
| 8,202,408 B2 | 6/2012 | Carson et al. |
| 8,246,799 B2 | 8/2012 | Oliver et al. |
| 8,324,914 B2 | 12/2012 | Chen et al. |
| 8,487,790 B2 | 7/2013 | Fife et al. |
| 8,628,649 B2 | 1/2014 | Lindsay et al. |
| 8,785,211 B2 | 7/2014 | Bayley et al. |
| 9,557,294 B2 * | 1/2017 | Chen .................. C12Q 1/6869 |
| 9,605,307 B2 | 3/2017 | Chen |
| 9,863,904 B2 | 1/2018 | Chen et al. |
| 11,112,375 B2 * | 9/2021 | Chen ................ G01N 27/44791 |
| 2004/0149580 A1 | 8/2004 | Flory |
| 2005/0019784 A1 | 1/2005 | Su et al. |
| 2005/0231855 A1 | 10/2005 | Tran |
| 2008/0311582 A1 | 12/2008 | Bayley et al. |
| 2009/0305273 A1 | 12/2009 | Cao et al. |
| 2010/0084276 A1 | 4/2010 | Lindsay |
| 2010/0122907 A1 | 5/2010 | Stanford et al. |
| 2010/0292101 A1 | 11/2010 | So et al. |
| 2010/0310421 A1 * | 12/2010 | Oliver ............. G01N 33/48721 422/82.01 |
| 2010/0331194 A1 | 12/2010 | Turner et al. |
| 2011/0050200 A1 | 3/2011 | Tartagni et al. |
| 2011/0192723 A1 | 8/2011 | Chen et al. |
| 2011/0193249 A1 * | 8/2011 | Chen ................ G01N 33/48721 264/4 |
| 2011/0193570 A1 * | 8/2011 | Chen ................ G01N 33/48721 324/654 |
| 2011/0224098 A1 | 9/2011 | Luan et al. |
| 2012/0052188 A1 | 3/2012 | Chen et al. |
| 2012/0219960 A1 | 8/2012 | Bayley et al. |
| 2013/0109577 A1 | 5/2013 | Korlach et al. |
| 2013/0118902 A1 | 5/2013 | Akeson et al. |
| 2013/0240359 A1 | 9/2013 | Turner et al. |
| 2013/0244340 A1 | 9/2013 | Davis et al. |
| 2013/0271164 A1 | 10/2013 | Savich |
| 2013/0341192 A1 | 12/2013 | Dunbar et al. |
| 2014/0027287 A1 | 1/2014 | Peng et al. |
| 2014/0083871 A1 | 3/2014 | Daniels |
| 2014/0134616 A1 * | 5/2014 | Davis .................. C12Q 1/6869 568/672 |
| 2014/0154790 A1 | 6/2014 | Ono et al. |
| 2014/0174927 A1 | 6/2014 | Bashir et al. |
| 2014/0190833 A1 | 7/2014 | Lieber et al. |
| 2014/0329225 A1 | 11/2014 | Morin |
| 2015/0107996 A1 | 4/2015 | Chen |
| 2016/0169865 A1 | 6/2016 | Rosenstein et al. |
| 2016/0245802 A1 | 8/2016 | Morin et al. |
| 2017/0022546 A1 | 1/2017 | Bashir |
| 2017/0074855 A1 | 3/2017 | Morin et al. |
| 2017/0083871 A1 | 3/2017 | Chang et al. |

FOREIGN PATENT DOCUMENTS

| | | |
|---|---|---|
| EP | 1951898 A1 | 8/2008 |
| EP | 2272981 A1 | 1/2011 |
| JP | 2009536107 | 10/2009 |
| JP | 2014-60997 | 4/2014 |
| WO | 2007057668 A1 | 5/2007 |
| WO | 2008042018 A2 | 4/2008 |
| WO | 2008092760 A1 | 8/2008 |
| WO | 2008124107 A1 | 10/2008 |
| WO | 2009045472 A1 | 4/2009 |
| WO | 2011097028 A1 | 8/2011 |
| WO | 2012/164679 A1 | 12/2012 |
| WO | 2012/178093 A1 | 12/2012 |
| WO | 2013109970 A1 | 7/2013 |
| WO | 2013130635 A2 | 9/2013 |
| WO | 2014/074727 A1 | 5/2014 |
| WO | 2014100693 A1 | 6/2014 |
| WO | 2015057324 A2 | 4/2015 |
| WO | 2015175789 A1 | 11/2015 |

OTHER PUBLICATIONS

Nicoli, F. et al., DNA Translocations through Solid-State Plasmonic Nanopores, Nano Letters, (2014), pp. 6917-6925, vol. 14 No. 12.

* cited by examiner

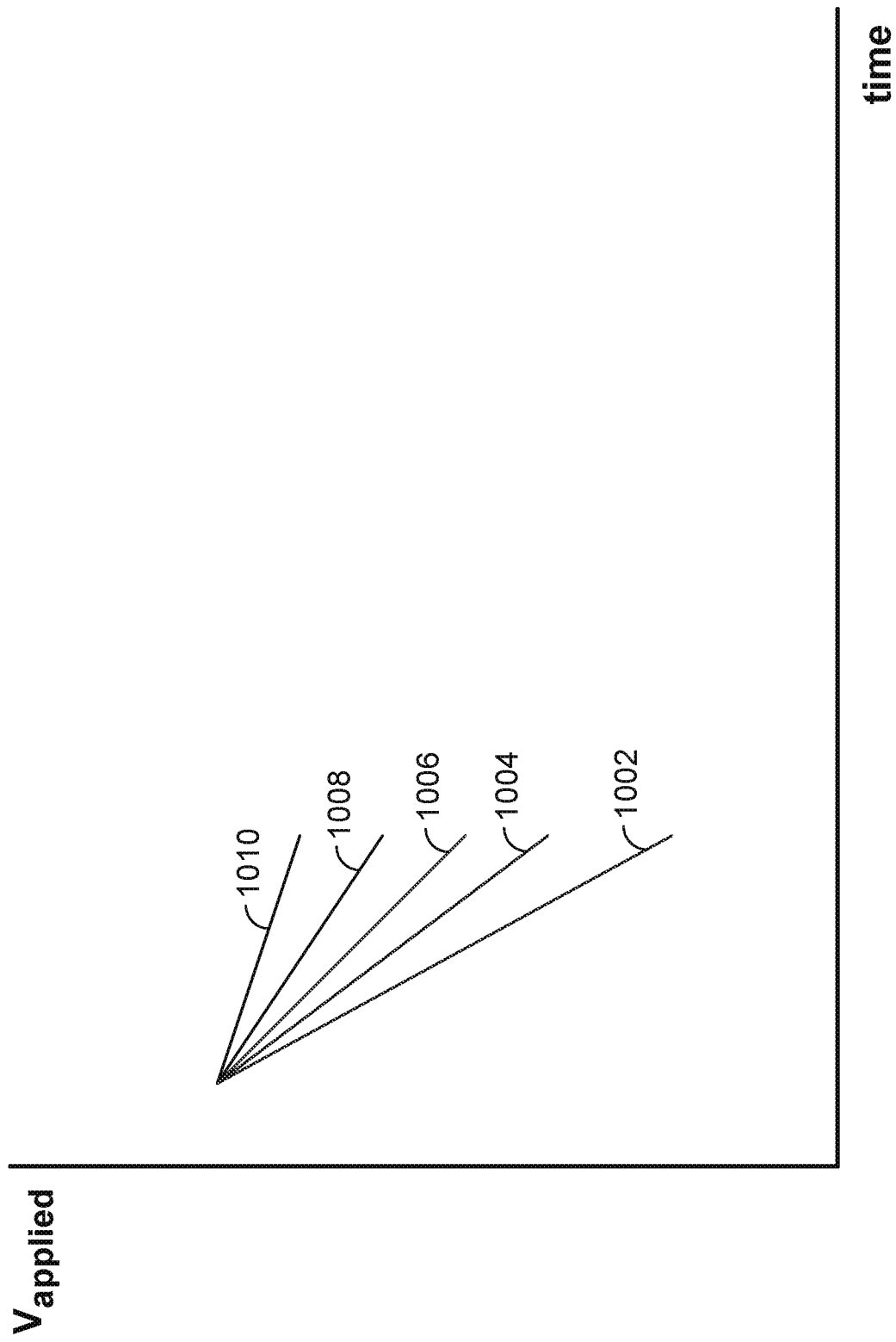

//NANOPORE-BASED SEQUENCING WITH VARYING VOLTAGE STIMULUS

CROSS REFERENCE TO OTHER APPLICATIONS

This application is a divisional of U.S. patent application Ser. No. 16/238,451, filed Jan. 2, 2019, now U.S. Pat. No. 11,150,216, which is a continuation of U.S. patent application Ser. No. 15/371,106, entitled NANOPORE-BASED SEQUENCING WITH VARYING VOLTAGE STIMULUS, filed Dec. 6, 2016, now U.S. Pat. No. 10,215,731, which is a continuation of U.S. patent application Ser. No. 14/577,511, now U.S. Pat. No. 9,557,294, entitled NANOPORE-BASED SEQUENCING WITH VARYING VOLTAGE STIMULUS, filed Dec. 19, 2016, each of which are incorporated herein by reference for all purposes.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

FIG. 10 illustrates an embodiment of the plots of the voltage applied across the nanopore versus time when the nanopore is in different states.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
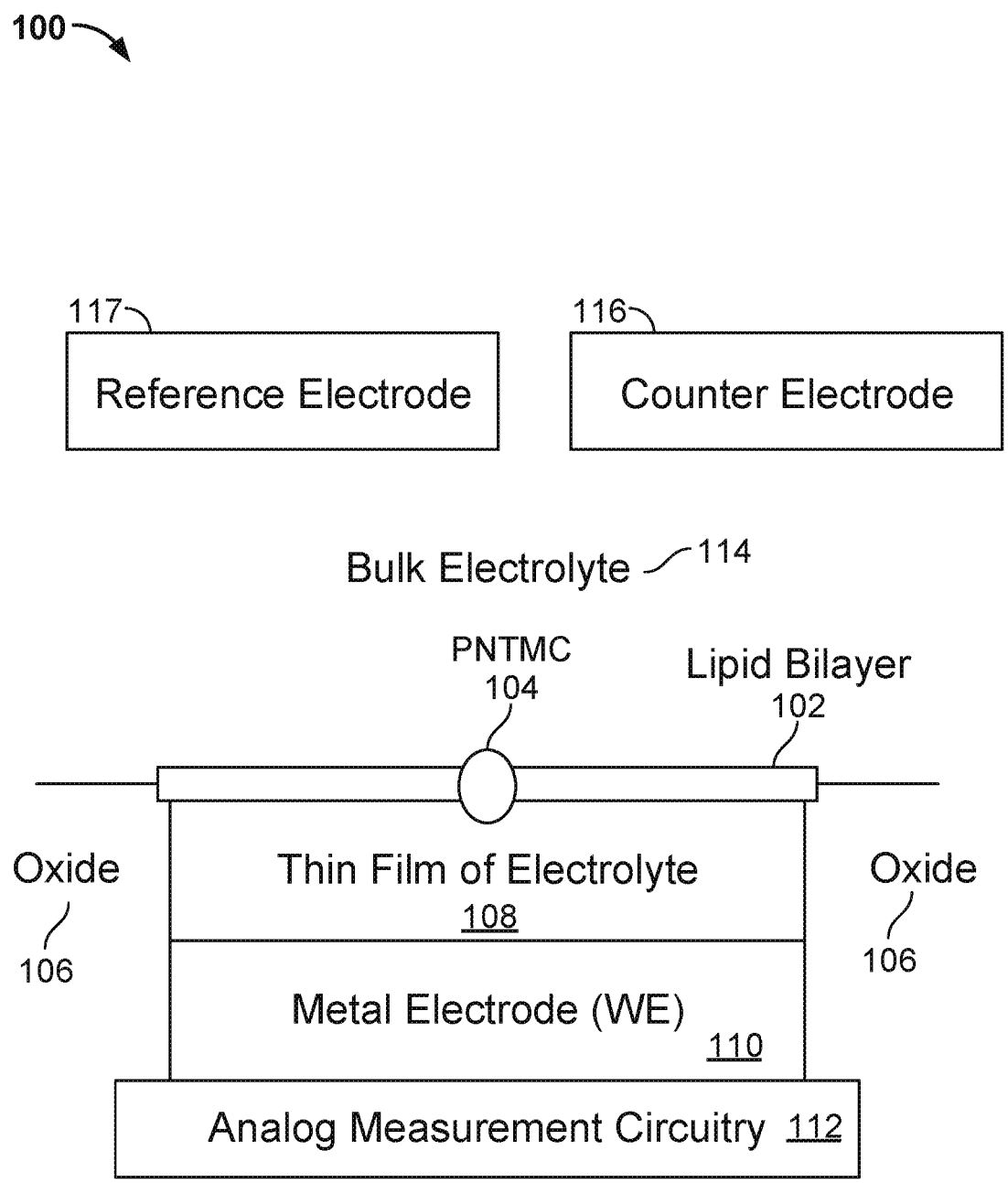
FIG. 1 illustrates an embodiment of a cell 100 in a nanopore based sequencing chip.

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing soluble protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is an electrochemical potential sensor. The cell also includes a reference electrode 117.

Figure 2:
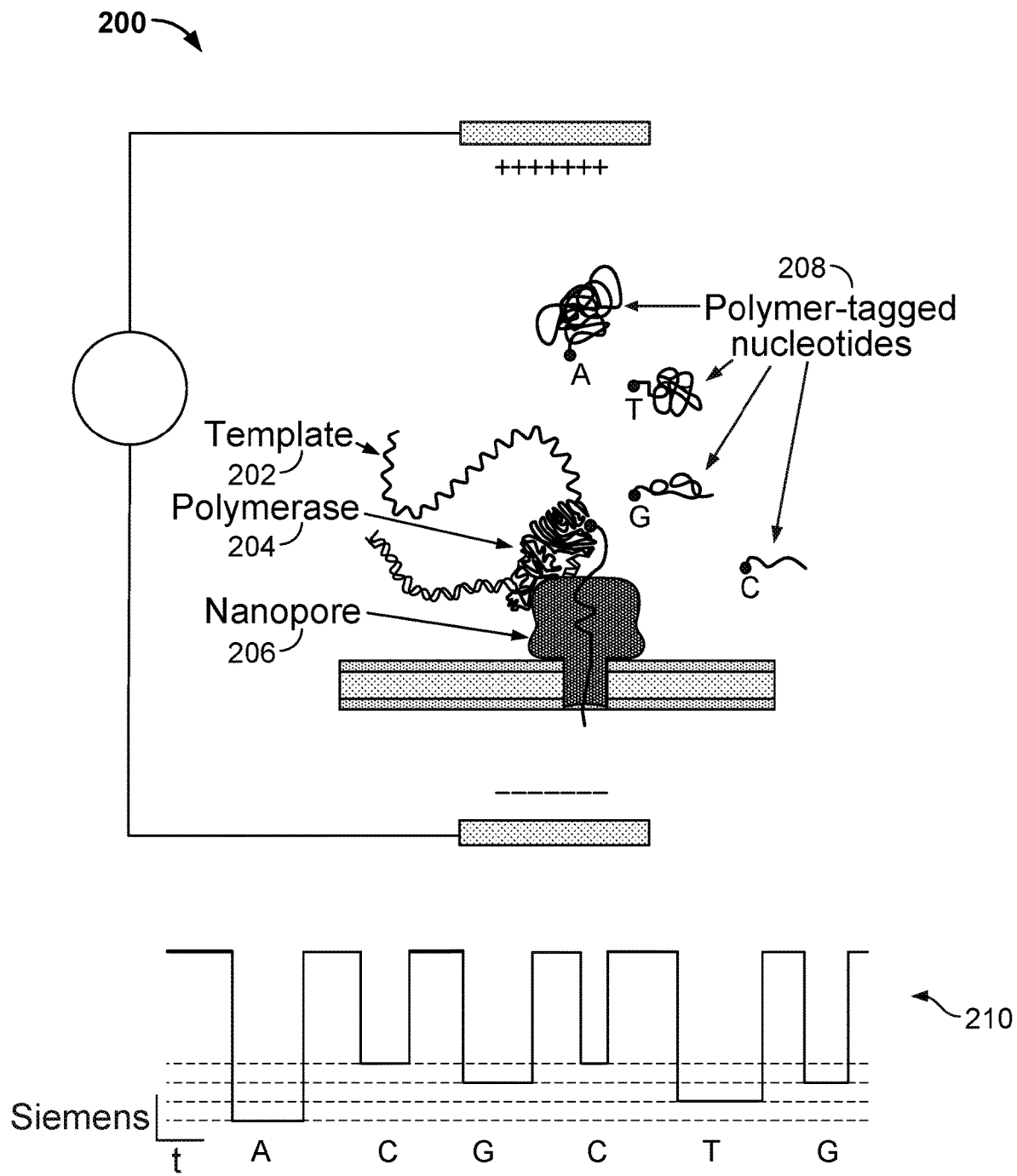
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
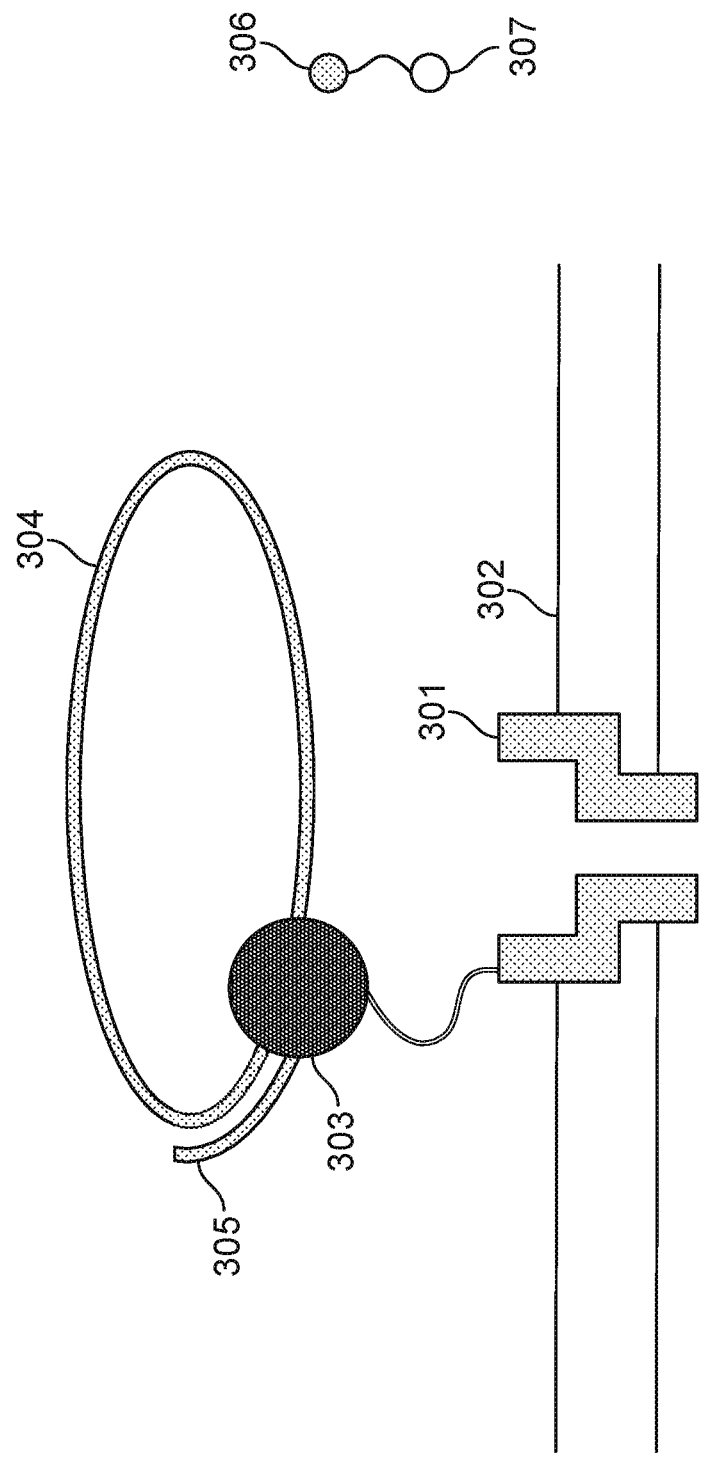
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
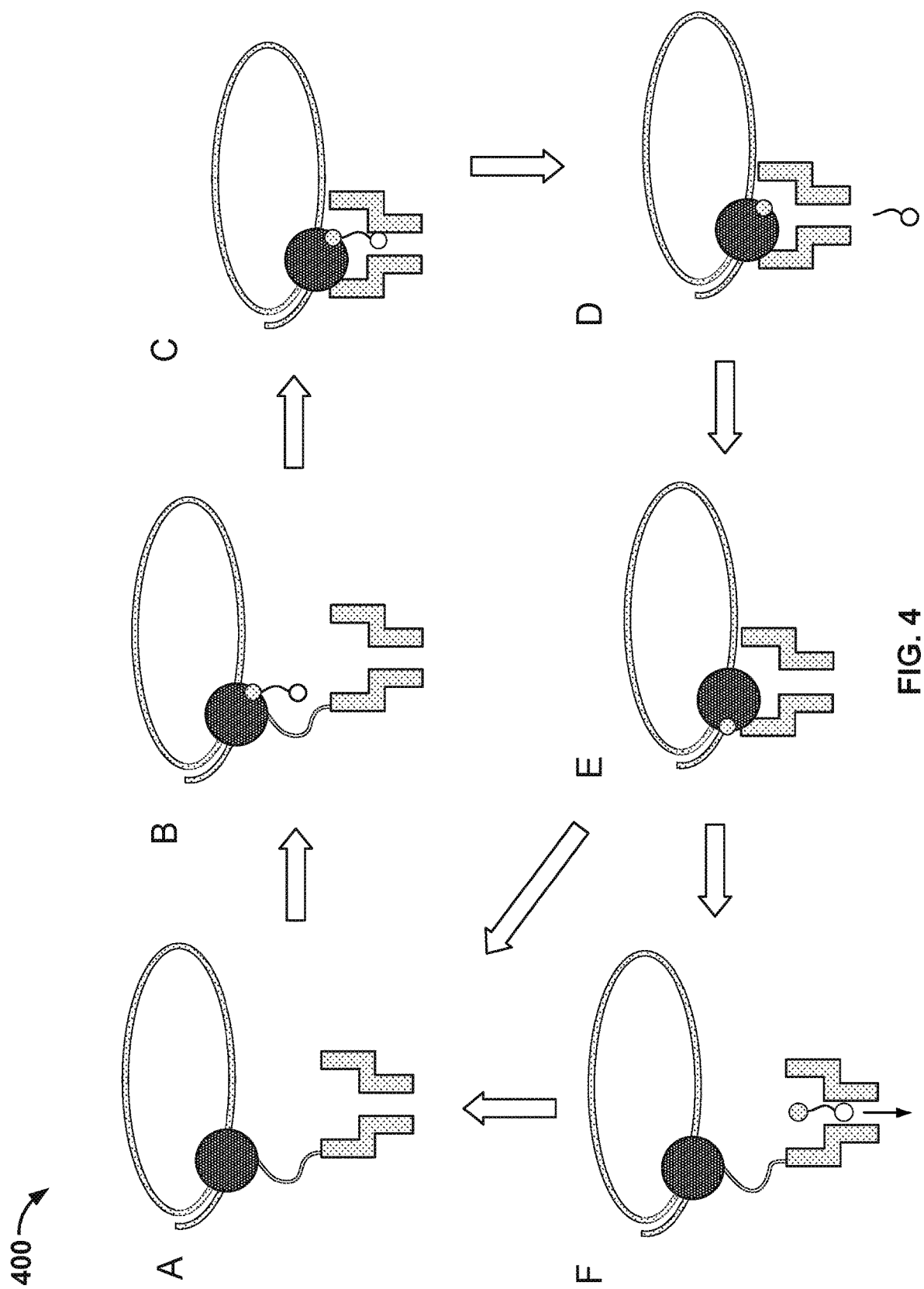
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 10000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the conductance of the nanopore is ~300 pico Siemens (300 pS). At stage C, the conductance of the nanopore is about 60 pS, 80 pS, 100 pS, or 120 pS corresponding to one of the four types of tagged nucleotides. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
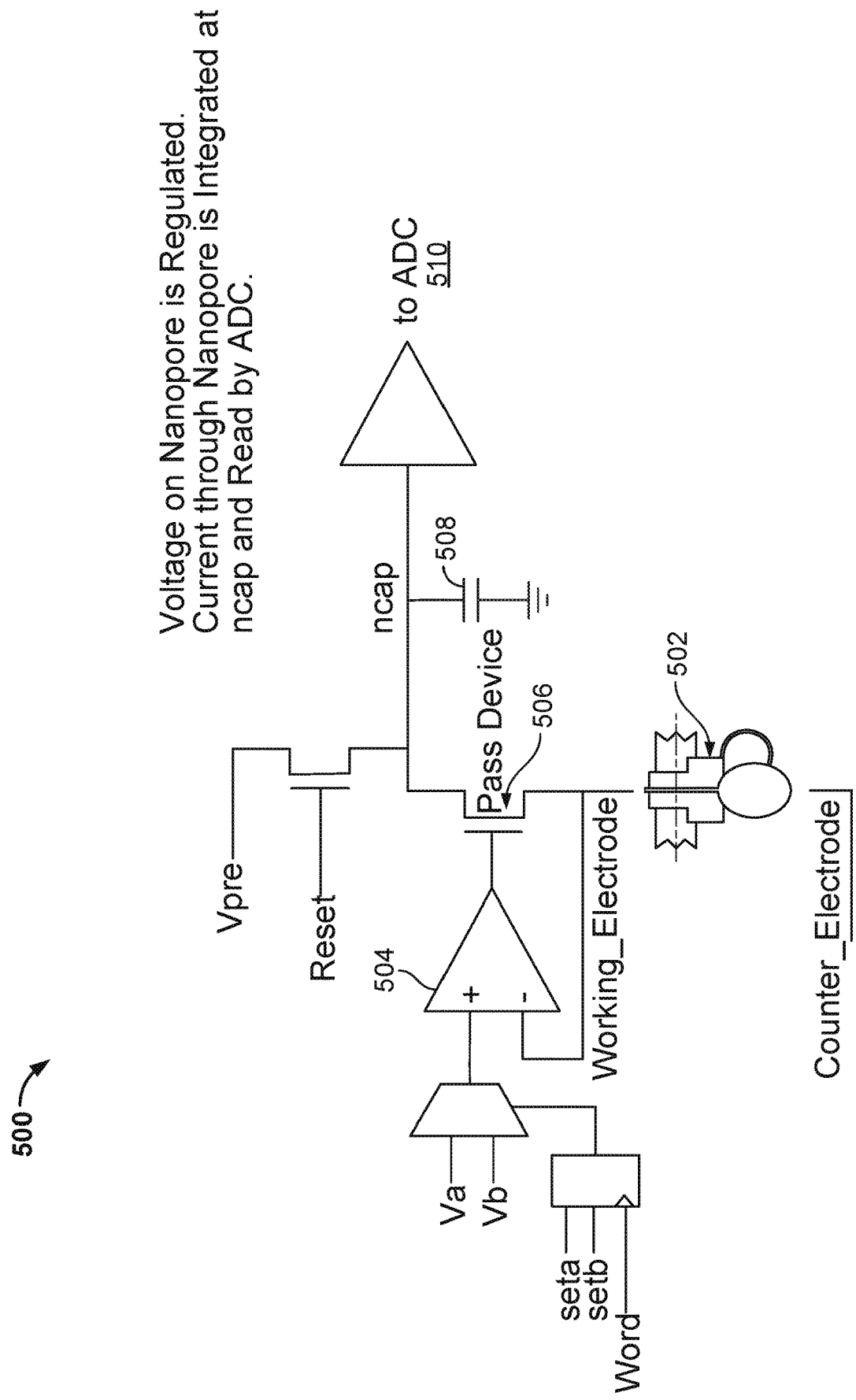
FIG. 5 illustrates an embodiment of a circuitry 500 in a cell of a nanopore based sequencing chip.

FIG. 5 illustrates an embodiment of a circuitry 500 in a cell of a nanopore based sequencing chip. As mentioned above, when the tag is held in nanopore 502, a unique conductance signal (e.g., see signal 210 in FIG. 2) is generated due to the tag's distinct chemical structures, thereby identifying the added base electronically. The circuitry in FIG. 5 maintains a constant voltage across nanopore 502 when the current flow is measured. In particular, the circuitry includes an operational amplifier 504 and a pass device 506 that maintain a constant voltage equal to $V_a$ or $V_b$ across nanopore 502. The current flowing through nanopore 502 is integrated at a capacitor $n_{cap}$ 508 and measured by an Analog-to-Digital (ADC) converter 510.

However, circuitry 500 has a number of drawbacks. One of the drawbacks is that circuitry 500 only measures unidirectional current flow. Another drawback is that operational amplifier 504 in circuitry 500 may introduce a number of performance issues. For example, the offset voltage and the temperature drift of operational amplifier 504 may cause the actual voltage applied across nanopore 502 to vary across different cells. The actual voltage applied across nanopore 502 may drift by tens of millivolts above or below the desired value, thereby causing significant measurement inaccuracies. In addition, the operational amplifier noise may cause additional detection errors. Another drawback is that the portions of the circuitry for maintaining a constant voltage across the nanopore while current flow measurements are made are area-intensive. For example, operational amplifier 504 occupies significantly more space in a cell than other components. As the nanopore based sequencing chip is scaled to include more and more cells, the area occupied by the operational amplifiers may increase to an unattainable size. Unfortunately, shrinking the operational amplifier's size in a nanopore based sequencing chip with a large-sized array may raise other performance issues. For example, it may exacerbate the offset and noise problems in the cells even further.

Figure 6:
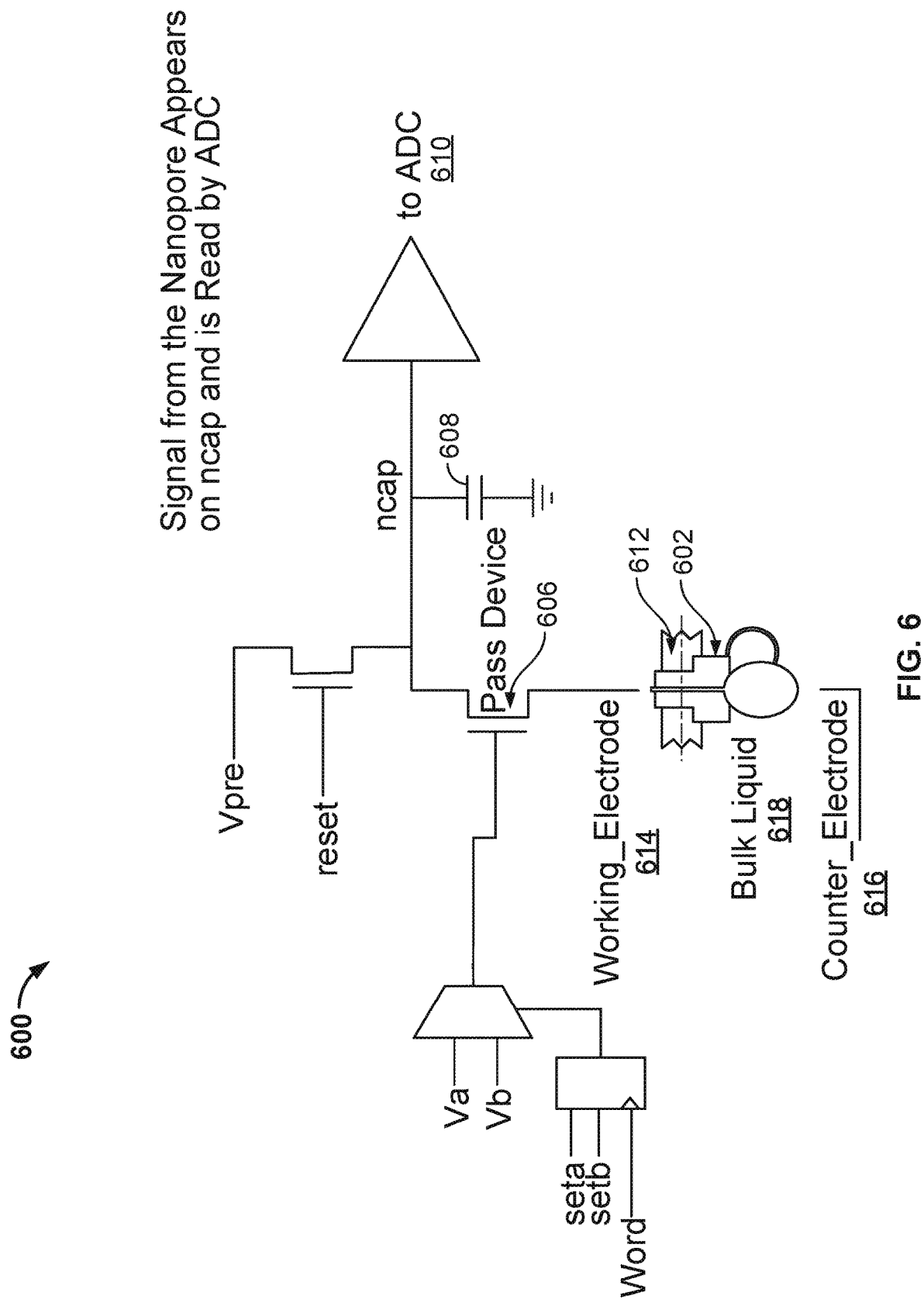
FIG. 6 illustrates an embodiment of a circuitry 600 in a cell of a nanopore based sequencing chip, wherein the voltage applied across the nanopore can be configured to vary over a time period during which the nanopore is in a particular detectable state.
Figure 7A:
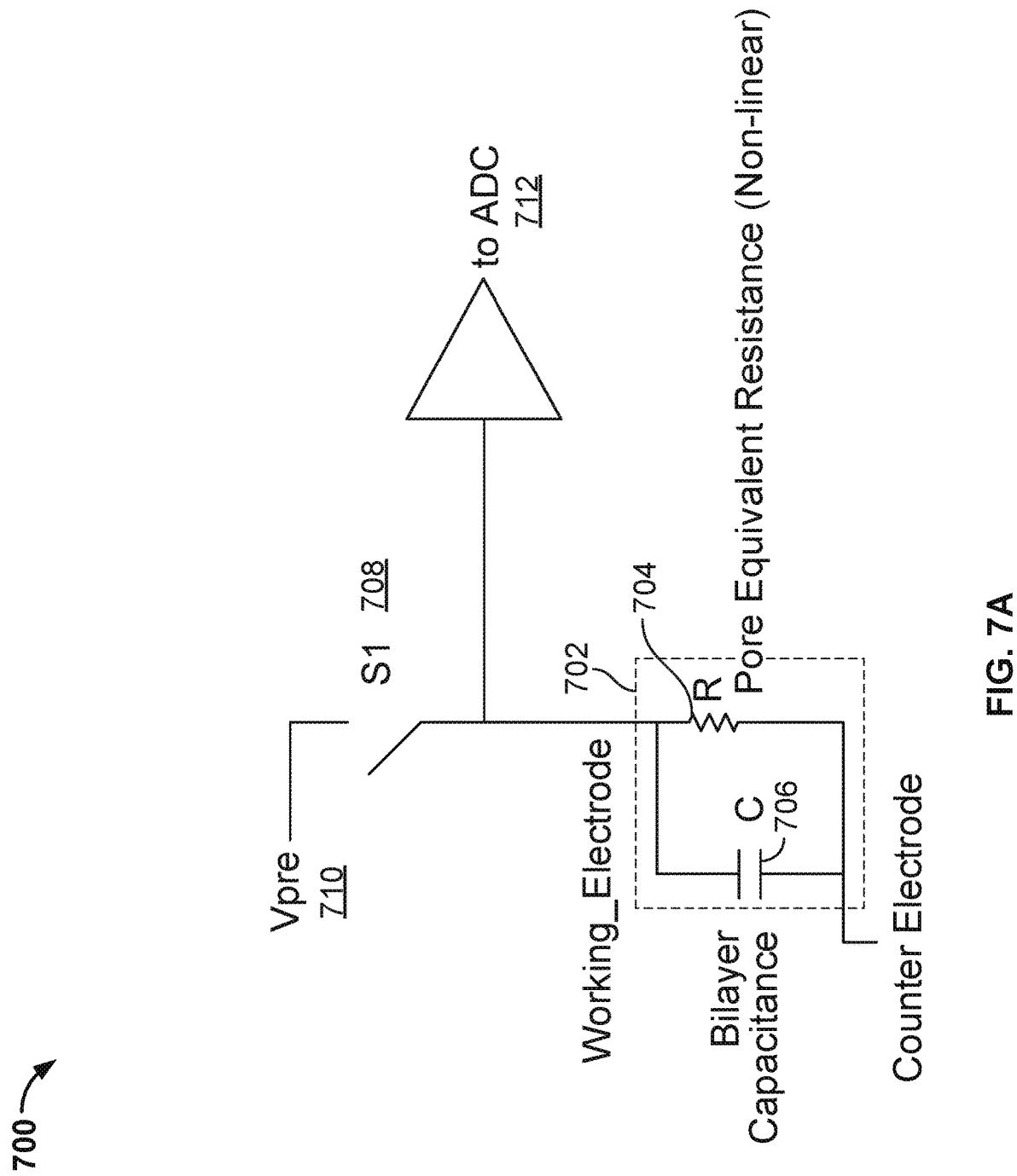
FIG. 7A illustrates an additional embodiment of a circuitry 700 in a cell of a nanopore based sequencing chip, wherein the voltage applied across the nanopore can be configured to vary over a time period during which the nanopore is in a particular detectable state.
Figure 7B:
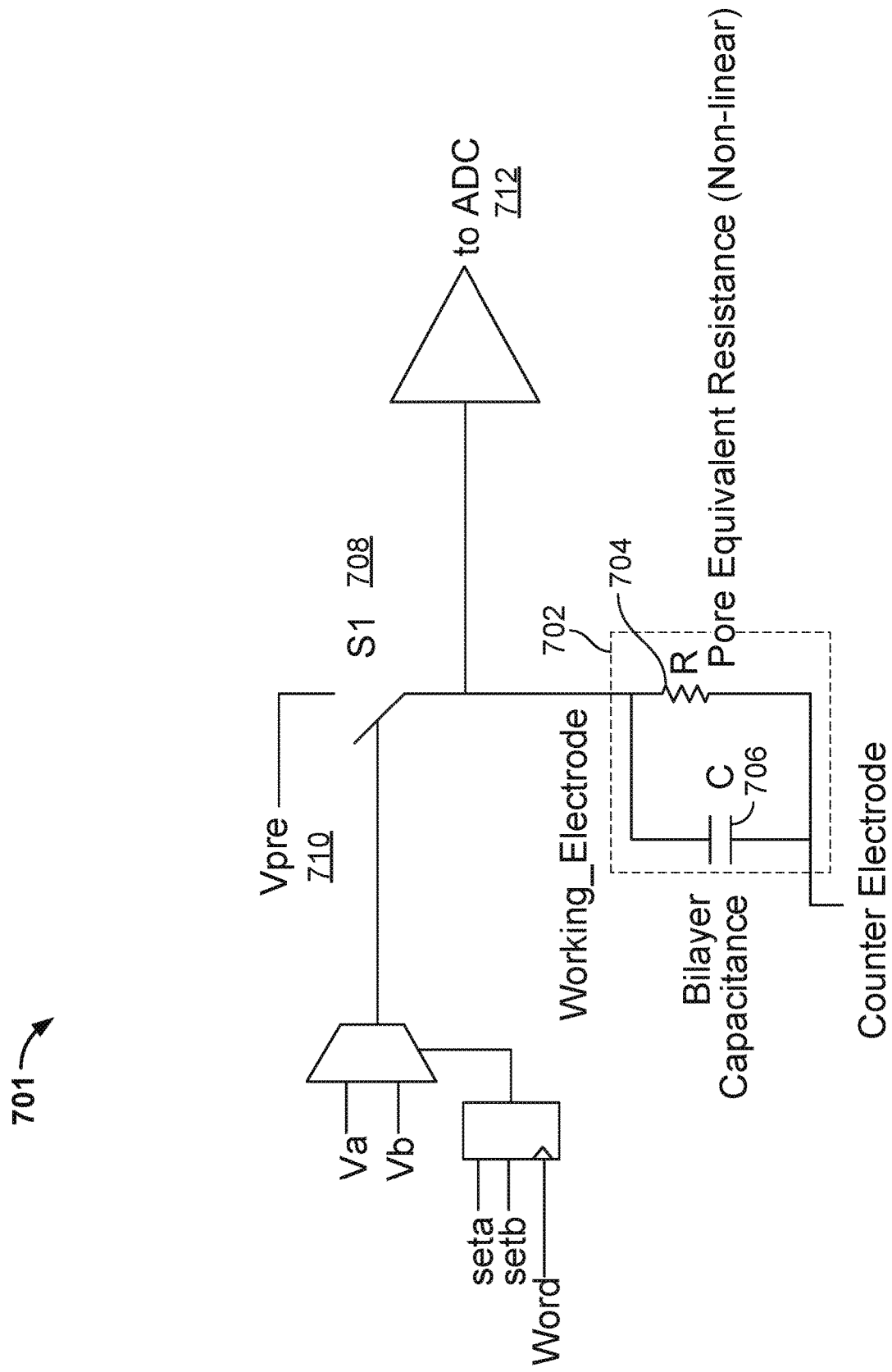
FIG. 7B illustrates an additional embodiment of a circuitry 701 in a cell of a nanopore based sequencing chip, wherein the voltage applied across the nanopore can be configured to vary over a time period during which the nanopore is in a particular detectable state.

FIG. 6 illustrates an embodiment of a circuitry 600 in a cell of a nanopore based sequencing chip, wherein the voltage applied across the nanopore can be configured to vary over a time period during which the nanopore is in a particular detectable state. One of the possible states of the nanopore is an open-channel state when a tag-attached polyphosphate is absent from the barrel of the nanopore. Another four possible states of the nanopore correspond to the states when the four different types of tag-attached polyphosphate (A, T, G, or C) are held in the barrel of the nanopore. Yet another possible state of the nanopore is when the membrane is ruptured. FIGS. 7A and 7B illustrate additional embodiments of a circuitry (700 and 701) in a cell of a nanopore based sequencing chip, wherein the voltage applied across the nanopore can be configured to vary over a time period during which the nanopore is in a particular detectable state. In the above circuits, the operational amplifier is no longer required.

FIG. 6 shows a nanopore 602 that is inserted into a membrane 612, and nanopore 602 and membrane 612 are situated between a cell working electrode 614 and a counter electrode 616, such that a voltage is applied across nanopore 602. Nanopore 602 is also in contact with a bulk liquid/electrolyte 618. Note that nanopore 602 and membrane 612 are drawn upside down as compared to the nanopore and membrane in FIG. 1. Hereinafter, a cell is meant to include at least a membrane, a nanopore, a working cell electrode, and the associated circuitry. In some embodiments, the counter electrode is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells. There is a working cell electrode within each measurement cell; in contrast to the common electrode, working cell electrode 614 is configurable to apply a distinct potential that is independent from the working cell electrodes in other measurement cells.

In FIGS. 7A and 7B, instead of showing a nanopore inserted in a membrane and the liquid surrounding the nanopore, an electrical model 702 representing the electrical properties of the nanopore and the membrane is shown. Electrical model 702 includes a capacitor 706 that models a capacitance associated with the membrane and a resistor 704 that models a resistance associated with the nanopore in different states (e.g., the open-channel state or the states corresponding to having different types of tag/molecule inside the nanopore). Note in FIGS. 7A and 7B that the respective circuitry does not require an extra capacitor (e.g., $n_{cap}$ 508 in FIG. 5) that is fabricated on-chip, thereby facilitating the reduction in size of the nanopore based sequencing chip.

Figure 8:
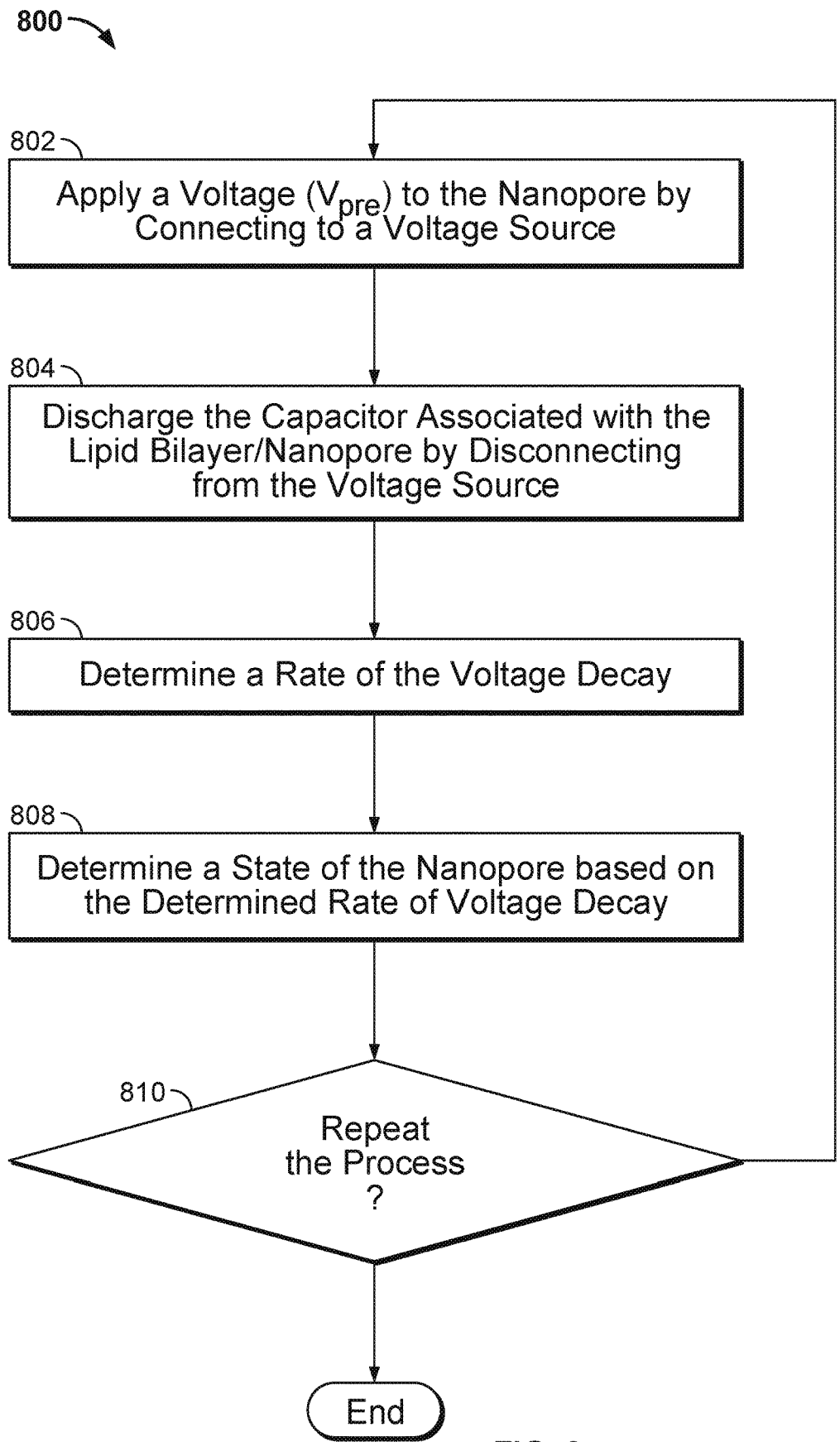
FIG. 8 illustrates an embodiment of a process 800 for analyzing a molecule inside a nanopore, wherein the nanopore is inserted in a membrane.
Figure 9:
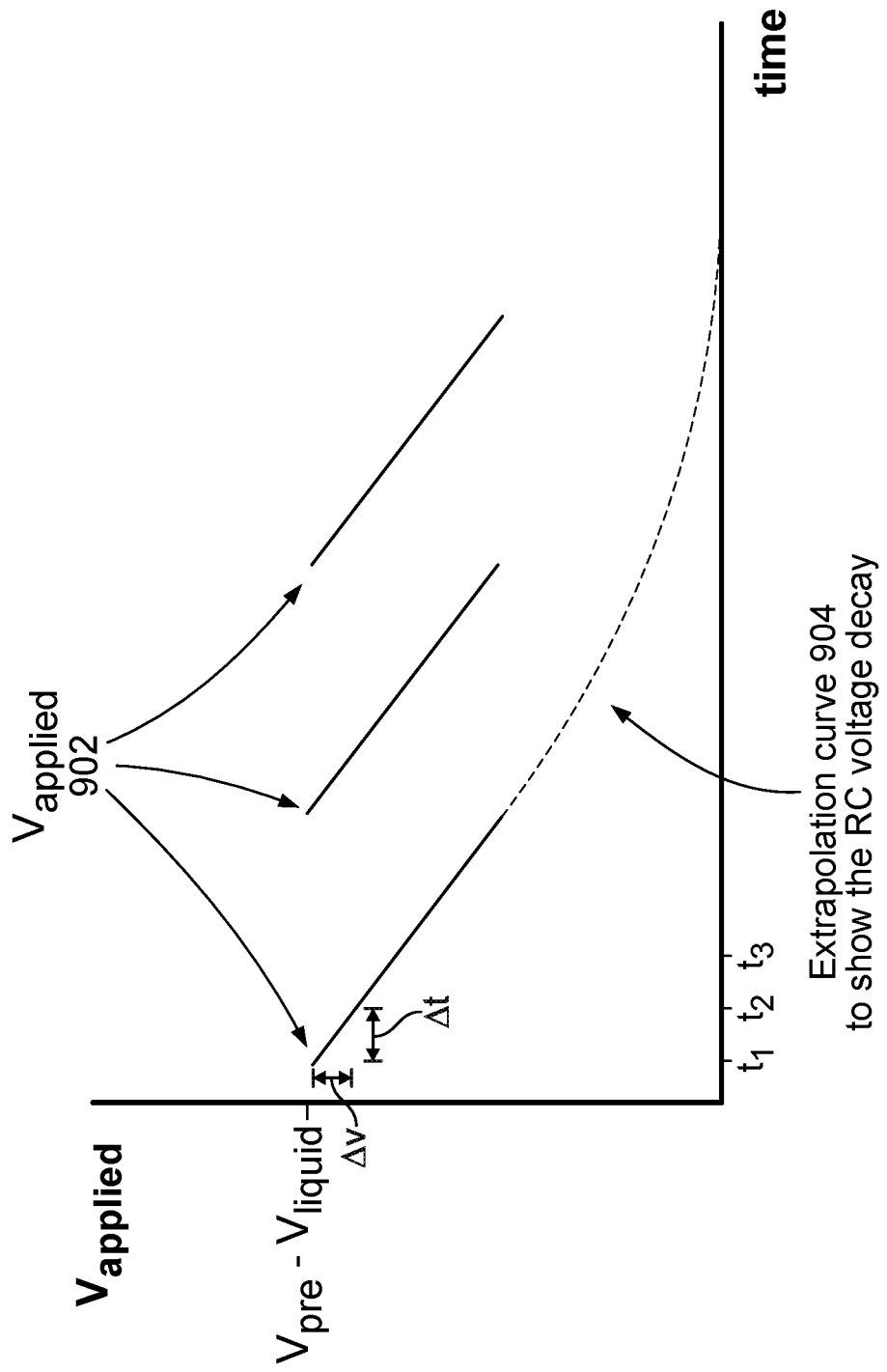
FIG. 9 illustrates an embodiment of a plot of the voltage applied across the nanopore versus time when process 800 is performed and repeated three times.

FIG. 8 illustrates an embodiment of a process 800 for analyzing a molecule inside a nanopore, wherein the nanopore is inserted in a membrane. Process 800 may be performed using the circuitries shown in FIG. 6, 7A, or 7B. FIG. 9 illustrates an embodiment of a plot of the voltage applied across the nanopore versus time when process 800 is performed and repeated three times. As will be described in greater detail below, the voltage applied across the nanopore is not held constant. In contrast, the voltage applied across the nanopore changes over time. The rate of the voltage decay (i.e., the steepness of the slope of the applied voltage across the nanopore versus time plot) depends on the cell resistance (e.g., the resistance of resistor 704 in FIG. 7A). More particularly, as the resistance associated with the nanopore in different states (e.g., the open-channel state, the states corresponding to having different types of tag/molecule inside the nanopore, and the state when the membrane is ruptured) are different due to the molecules'/tags' distinct chemical structure, different corresponding rates of voltage decay may be observed and thus may be used to identify the different states of the nanopore.

With reference to FIG. 8 and FIG. 7A, at 802 of process 800, a voltage is applied across the nanopore by coupling the nanopore to a voltage source. For example, as shown in FIG. 7A, a voltage $V_{pre}$ 710 is applied to the cell working electrode when a switch S1 708 is closed. As shown in FIG. 9, the initial voltage applied across the nanopore is $V_{pre}-V_{liquid}$, where $V_{liquid}$ is the voltage of the bulk liquid in contact with the nanopore. As the voltage source is connected to the working electrode, the capacitor associated with the membrane is charged and energy is stored in an electric field across the membrane.

At 804 of process 800, the capacitor associated with the membrane (capacitor 706) is discharged by decoupling the nanopore and the membrane from the voltage source, and the energy stored in the electric field across the membrane is thereby dissipated. For example, as shown in FIG. 7A, the voltage source is disconnected when switch S1 708 is opened. After switch S1 708 is opened, the voltage across the nanopore begins to decay exponentially, as shown in FIG. 9. The exponential decay has a RC time constant $\tau=RC$, where R is the resistance associated with the nanopore (resistor 704) and C is the capacitance associated with the membrane (capacitor 706) in parallel with R.

At 806 of process 800, a rate of the decay of the voltage applied across the nanopore is determined. The rate of the voltage decay is the steepness of the slope of the applied voltage across the nanopore versus time curve, as shown in FIG. 9. The rate of the voltage decay may be determined in different ways.

In some embodiments, the rate of the voltage decay is determined by measuring a voltage decay that occurs during a fixed time interval. For example, as shown in FIG. 9, the voltage applied at the working electrode is first measured by ADC 712 at time $t_1$, and then the voltage is again measured by ADC 712 at time $t_2$. The voltage difference $\Delta V_{applied}$ is greater when the slope of the voltage across the nanopore versus time curve is steeper, and the voltage difference $\Delta V_{applied}$ is smaller when the slope of the voltage curve is less steep. Thus, $\Delta V_{applied}$ may be used as a metric for determining the rate of the decay of the voltage applied across the nanopore. In some embodiments, to increase the accuracy of the measurement of the rate of voltage decay, the voltage may be measured additional times at fixed intervals. For example, the voltage may be measured at $t_3$, $t_4$, and so on, and the multiple measurements of $\Delta V_{applied}$ during the multiple time intervals may be jointly used as a metric for determining the rate of the decay of the voltage applied across the nanopore. In some embodiments, to increase the accuracy of the measurement of the rate of voltage decay, correlated double sampling (CDS) may be used.

In some embodiments, the rate of the voltage decay is determined by measuring a time duration that is required for a selected amount of voltage decay. In some embodiments, the time required for the voltage to drop from a fixed voltage $V_1$ to a second fixed voltage $V_2$ may be measured. The time required is less when the slope of the voltage curve is steeper, and the time required is greater when the slope of the voltage curve is less steep. Thus, the measured time required may be used as a metric for determining the rate of the decay of the voltage applied across the nanopore.

At 808 of process 800, a state of the nanopore is determined based on the determined rate of voltage decay. One of the possible states of the nanopore is an open-channel state during which a tag-attached polyphosphate is absent from the barrel of the nanopore. Other possible states of the nanopore correspond to the states when different types of molecules are held in the barrel of the nanopore. For example, another four possible states of the nanopore correspond to the states when the four different types of tag-attached polyphosphate (A, T, G, or C) are held in the barrel of the nanopore. Yet another possible state of the nanopore is when the membrane is ruptured. The state of the nanopore can be determined based on the determined rate of voltage decay, because the rate of the voltage decay depends on the cell resistance; i.e., the resistance of resistor 704 in FIG. 7A. More particularly, as the resistance associated with the nanopore in different states are different due to the molecules/tags' distinct chemical structure, different corresponding rates of voltage decay may be observed and thus may be used to identify the different states of the nanopore.

FIG. 10 illustrates an embodiment of the plots of the voltage applied across the nanopore versus time when the nanopore is in different states. Curve 1002 shows the rate of voltage decay during an open-channel state. In some embodiments, the resistance associated with the nanopore in an open-channel state is in the range of 100 Mohm to 20 Gohm. Curves 1004, 1006, 1008, and 1010 show the different rates of voltage decay corresponding to the four capture states when the four different types of tag-attached polyphosphate (A, T, G, or C) are held in the barrel of the nanopore. In some embodiments, the resistance associated with the nanopore in a capture state is within the range of 200 Mohm to 40 Gohm. Note that the slope of each of the plots is distinguishable from each other.

At 810 of process 800, it is determined whether process 800 is repeated. For example, the process may be repeated a plurality of times to detect each state of the nanopore. If the process is not repeated, then process 800 terminates; otherwise, the process restarts at 802 again. At 802, a voltage is reasserted across the nanopore by connecting to the voltage source. For example, as shown in FIG. 7A, a voltage $V_{pre}$ 710 is applied across the nanopore when switch S1 708 is closed. As shown in FIG. 9, the applied voltage jumps back up to the level of $V_{pre}$. As process 800 is repeated a plurality of times, a saw-tooth like voltage waveform is applied across the nanopore over time. FIG. 9 also illustrates an extrapolation curve 904 showing the RC voltage decay over time had the voltage $V_{pre}$ 710 not been reasserted.

As shown above, configuring the voltage applied across the nanopore to vary over a time period during which the nanopore is in a particular detectable state has many advantages. One of the advantages is that the elimination of the operational amplifier, the pass device, and the capacitor (e.g., $n_{cap}$ 508 in FIG. 5) that are otherwise fabricated on-chip in the cell circuitry significantly reduces the footprint of a single cell in the nanopore based sequencing chip, thereby facilitating the scaling of the nanopore based sequencing chip to include more and more cells (e.g., having millions of cells in a nanopore based sequencing chip). The capacitance in parallel with the nanopore includes two portions: the capacitance associated with the membrane and the capacitance associated with the integrated chip (IC). Due to the thin nature of the membrane, the capacitance associated with the membrane alone can suffice to create the required RC time constant without the need for additional on-chip capacitance, thereby allowing significant reduction in cell size and chip size.

Another advantage is that the circuitry of a cell does not suffer from offset inaccuracies because $V_{pre}$ is applied directly to the working electrode without any intervening circuitry. Another advantage is that since no switches are being opened or closed during the measurement intervals, the amount of charge injection is minimized.

Furthermore, the technique described above operates equally well using positive voltages or negative voltages. Bidirectional measurements have been shown to be helpful in characterizing a molecular complex. In addition, bidirectional measurements are required when the type of ionic flow that is driven through the nanopore is via non-faradaic conduction. Two types of ionic flow can be driven through the nanopore—faradaic conduction and non-faradaic conduction. In faradaic conduction, a chemical reaction occurs at the surface of the metal electrode. The faradaic current is the current generated by the reduction or oxidation of some chemical substances at an electrode. The advantage of non-faradaic conduction is that no chemical reaction happens at the surface of the metal electrode.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for analyzing a molecule, the system comprising:
   a well having an opening configured to support a membrane having a nanopore disposed therein;
   a working electrode disposed within the well;
   a counter electrode located outside the well such that the membrane, when formed over the opening of the well, is located between the working electrode and the counter electrode;
   a voltage source in electrical communication with the working electrode, wherein the working electrode in connection with the voltage source and counter electrode are configured to apply an applied voltage between the working electrode and the counter electrode;
   a measuring circuit configured to measure a change in a measured voltage in response to the applied voltage between the working electrode and the counter electrode; and
   a processor configured to determine a rate of change in the measured voltage and to distinguish the molecule in the nanopore from other possible molecules based at least in part on the determined rate of change in the measured voltage.

2. The system in claim 1, wherein the processor is configured to distinguish the molecule in the nanopore from other possible molecules based at least in part on the determined rate of change in the measured voltage that occurs in response to a reduction in the applied voltage that is applied between the working electrode and the counter electrode.

3. The system of claim 1, further comprising a switch between the working electrode and the voltage source.

4. The system of claim 1, wherein the measuring circuit does not include an operational amplifier.

5. The system of claim 1, wherein the measuring circuit is configured to measure the change in the measured voltage over a predetermined duration.

6. The system of claim 1, wherein the measuring circuit is configured to measure an amount of time needed to achieve a predetermined change in the measured voltage.

7. The system of claim 1, wherein the molecule is a tag attached to a nucleotide.

\* \* \* \* \*